US006303329B1

(12) United States Patent
Heinrikson et al.

(10) Patent No.: US 6,303,329 B1
(45) Date of Patent: Oct. 16, 2001

(54) METHOD FOR AUTOACTIVATION OF PROCASPASE 8

(75) Inventors: Robert Leroy Heinrikson, Plainwell; Alfredo Giuseppe Tomasselli; Kenneth A. Koeplinger, both of Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/360,017

(22) Filed: Jul. 23, 1999

Related U.S. Application Data

(60) Provisional application No. 60/094,238, filed on Jul. 27, 1998.

(51) Int. Cl.$^7$ .............................. C12Q 1/37; C12N 9/50; C12P 21/06
(52) U.S. Cl. ........................... 435/68.1; 435/219; 435/23
(58) Field of Search .............................. 435/23, 68.1, 219

(56) References Cited

U.S. PATENT DOCUMENTS

| 5,712,115 | 1/1998 | Hawkins et al. | 435/69.1 |
| 5,786,173 | 7/1998 | Alnemri et al. | 435/69.1 |
| 5,851,815 | 12/1998 | Alnemri et al. | 435/219 |
| 6,008,042 | 12/1999 | Dixit et al. | 435/325 |

FOREIGN PATENT DOCUMENTS

WO 97/03998    2/1997  (WO) .

OTHER PUBLICATIONS

AM Chinnaiyan, VM Dixit, "The cell–death machine," *Current Biology* 6, pp. 555–562 (1996).
T Fernandes–Alnemri, G Litwack, ES Al nemri, Mch2, a New Member of the Apoptotic Ced–3/Ice Cysteine Protease Gene Family, *Cancer Research* 55 , pp. 2737–2742 (1995).
DM Holtzman, Mohanish Deshmukh, "Caspases: A treatment target for neurodegenerative disease?" *Nature Medicine* 3, pp. 954–955 (1997).
N Margolin, et al., "Substrate and Inhibitor Specificity of Interleukin 1 β–converting Enzyme and Related Caspases," *J Biol Chem* 272, pp. 7223–7228 (1997).
DA Martin, et al., "Membrane Oligomerization and Cleavage Activates the Caspase–8 (FLICE/MACH•1) Death Signal," *J Biol Chem* 273, pp. 4345–4349 (1998).

MP Mattson,, et al., "Presenilins, the Endoplasmic Reticulum, and Neuronal Apoptisis in Alzheimer's Disease," *J. Neurochem* 70, pp. 1–14 (1998).
JP Medema, et al., "FLICE is activated by association with the CD95 death–inducing signaling complex (DISC)," *The EMBO Journal*, vol. 16, No. 10, pp. 2794–2804 (1997).
DK Miller, J Myerson, JW Becker, "The Interleukin–1β Converting Enzyme Famile of Cysteine Proteases," *J Cel, Biochem* 64, 2–10 (1997).
M Muzio, et al., "An Induced Proximity Model for Caspase–8 Activation,"*J. Biol Chem* 273, pp. 2926–2930 (1998).
M Muzio, GS Salvesen, VM Dixit, "Flice Induced Apoptosis in a Cell–free System," *J Biol Chem* 272, pp. 2952–2956.
DW Nicholson, NA Thornberry, "Caspases: killer proteases," *TIBS* 22, pp. 299–306 (1997).
K Orth, et al., "Molecular Ordering of Apoptotic Mannalian CED–3/ICE–like Proteases," *J Biol Chem* 271, pp. 20977–20980 (1996).
HR Stennicke, GS Salvesen, "Biochemical Characteristics of Caspases–3, –6, –7, and –8," *J Biol Chem* 272, pp. 25719–25723 (1997).
SM Srinivasula, et al., "Molecular ordering of the Fas–apoptotic pathway: The Fas/APO–1 protease Mch5 is a CrmA–inhibitable protease that activates multiple Ced–3/ICE–like cysteine proteases," *Proc, Natl. Acad. Sci* 93, pp. 14486–14491 (1996).
J Sun, et al., "Recombinant Caspase–3 Expressed in *Pichia pastoris* is Fully Activated, and Kinetically Indistinguishabe from the Native Enzyme," *Biochem Biophys Res Comm* 238, pp. 920–924 (1997).
RV Talanian, et al., "Substrate Specificities of Caspase Family Proteases,"*J Biol. Chem* 272, *J Biol Chem* 272, pp. 9677–9682 (1997).
NA Thornberry, et al., "A Combinatorial Approach Defines Specificities of Members of the Caspase Family and Granzyme B,"*J Biol. Chem* 272, pp. 17907–17911 (1997).
Q Zhou, et al, "Target Protease Specificity of the Viral Serpin CrmA," *J Biol. Chem* 272, pp. 7797–7800 (1997).

Primary Examiner—Rebecca E. Prouty
Assistant Examiner—M Monshipouri
(74) *Attorney, Agent, or Firm*—Thomas A. Wootton

(57) ABSTRACT

A novel recombinant procaspase 8 protein lacking the death effector domains and a method for converting said novel procaspase protein to full active human caspase 8 by concentration of the procaspase 8 on a collection device.

2 Claims, 7 Drawing Sheets

(1 of 7 Drawing Sheet(s) Filed in Color)

Figure 2

```
  1 MRGSHHHHHH GSMTISDSPR EQDSESQTLD KVYQMKSKPR GYCLIINNHN
 51 FAKAREKVPK LHSIRDRNGT HLDAGALTTT FEELHFEIKP HDDCTVEQIY
101 EILKIYQLMD HSNMDCFICC ILSHGDKGII YGTDGQEAPI YELTSQFTGL
151 KCPSLAGKPK VFFIQACQGD NYQKGIPVET DSEEQPYLEM DLSSPQTRYI
201 PDEADFLLGM ATVNNCVSYR NPAEGTWYIQ SLCQSLRERC PRGDDILTIL
251 TEVNYEVSNK DDKKNMGKQM PQPTFTLRKK LVFPSD
```

METHOD FOR AUTOACTIVATION OF PROCASPASE 8

CROSS-REFERENCE TO RELATED APPLICATIONS

This application claims the benefit of the following provisional application: U.S. Ser. No. 60/094,238, filed Jul. 27, 1998, under USC 119(e)(1).

BACKGROUND OF INVENTION

1. Field of Invention

The present invention is a method for converting recombinant procaspase 8 protein to active human caspase 8 enzyme and a method of producing the recombinant protein.

2. Related Art

The caspases are a family of related cysteinyl proteinases which play important intracellular roles in inflammation and apoptosis. See, for example, D. W. Nicholson et al., TIBS 22: 299–306 (1997). Members of this proteinase family share a number of features in common. They all employ a conserved cysteine residue as the nucleophile for attack on peptide bonds, and the sites of cleavage all show Asp in the $P_1$ position of the peptide substrates (A. C. Chinnayan et al., Current Biol. 6, 555–562 (1996)). The catalytic domain of the caspases has a mass of roughly 30 kDa and comprises two polypeptide chains, a 20 kDa N-terminal a fragment which contains the active site Cys, and a 10 kDa C-terminal β peptide which contributes to the formation of the active site. These chains arise by internal cleavage of a single-chain zymogen precursor, and are tightly associated in an αβ heterodimer. Proteolytic processing which gives rise to these component polypeptides may be autocatalytic (H. R. Stennicke et al., J. Biol. Chem. 272, 25719–25723 (1997)), or can be mediated by other caspases or by enzymes of similar specificity, for example, granzyme B, a lymphocyte enzyme with a specificity for $P_1$ Asp similar to that of the caspases (C. J. Froelich et al., Nature Medicine 3: 954–55 (1997)).

As with nearly all proteolytic enzymes, the caspases exist as inactive precursors, or proenzymes. The length of the N-terminal prodomains of the caspases vary considerably depending on how activation is regulated. Our present invention focuses on caspase 8 which is involved in apoptosis. The structure of the proenzyme, or zymogen form of this protein is illustrated schematically in FIG. 1. The N-terminal prosegment in caspase 8, contains two death-effector domains (DED). Immunoprecipitation experiments of activated death-initiation signaling complexes (DISC) show that procaspase 8 is a component of the activated receptor complexes (M. Muzio et al., J. BioL Chem. 273, 2926–2930 (1996)). Because of sequence homology between the death effector domains of procaspase 8 and the death domains (DD) of FADD and TRADD, the death domain proteins associated with TNF and Fas receptors (J. P. Medema et al., EMBO Journal 16, 2794–2804 (1997)), the regions of homology are thought to result in the selective association or recruitment of procaspase 8 to the activated receptors. As a component of activated DISC, procaspase 8 plays a key role in the direct line of signal transduction, and activation of the Fas or TNF receptors with Fas ligand or TNF results in its autocatalytic, intermolecular activation. Activated caspase 8 is then thought to activate other, downstream caspases, like caspase 3, which have prosegments that are shorter and whose intracellular concentrations are not high enough to support their autocatalytic processing and activation. Thus, caspase 8 has been suggested to sit at the apex of the Fas or TNF mediated apoptotic cascade and likely serves as the prime mover for activation of the "executioners" of apoptosis whose function is to destroy critical cellular proteins (D. W. Nicholson et al., see above).

Because of its initiating role in Fas or TNF mediated apoptosis, caspase 8 is believed to be a viable target in blockade of the undesirable cell death which occurs in a variety of neurological disorders. See, for example, M. P. Mattson et al., J. Neurochem. 70, 1–14 (1998)). In view of the biological significant role of caspase 8 in the apoptotic process and the need to further elucidate the role and mechanism of action of this protein in the cell death process the need for a reproducible method for the production of active protein has become very important.

The current belief that the death-effector domains provide the mechanism for recruitment of procaspase 8 to the cell membrane is consistent with our finding that given a sufficiently high concentration of the catalytic domain of the protein in solution, it is possible to affect autoactivation of a truncated procaspase 8 construct missing the DED.

Information Disclosure

References relating to caspase 8: M. Muzio et al., J. BioL Chem. 272, 2952–2956 (1997); H. R. Stennicke et al., J. Biol. Chem. 272, 25719–25723 (1997); Q. Zhou et al., J. Biol. Chem. 272, 7797–7800 (1997); D. A. Martin et al., J. Biol. Chem. 273, 4345–4349 (1998); and M. Muzio et al., J. Biol. Chem. 273, 2926–2930 (1998).

Other caspase references: J. Sun et al., Biochem. Biophys. Res. Comm. 238, 920–924 (1997); D. K Miller et al., J. Cell. Biochem. 64, 2–10 (1997); N. Margolin et al., J. Biol. Chem. 272, 7223–7228 (1997); R V. Talanian et al., J. Biol. Chem. 272, 9677–9682 (1997); N. A. Thornberry et al., J. Biol. Chem. 272, 17907–17911 (1997); K. 0111 et al, J. Biol. Chem. 271, 2097720980 (1996); and T. Fernandes-Alnemri et al., Cancer Res. 55, 2737–2742 (1995).

SUMMARY OF INVENTION

The present invention provides a novel recombinant procaspase 8 protein molecule the amino acid sequence of which is shown in FIG. 2 and more specifically in SEQ ID NO: 1. The cDNA construct (SEQ ID NO: 2) used to express the novel recombinant procaspase 8 protein is also a part of the present invention.

The present invention also provides a method for the quantitative and reproducible conversion of the recombinant procaspase 8 protein to active human caspase 8, with a recovery of 50 to 75%. In the method of the present invention a buffered solution, pH 8, of the recombinant procaspase 8 protein is passed through a matrix thereby concentrating the protein on the matrix surface to create an environment favorable to autoactivation of the protein. In a preferred embodiment of the present invention the matrix is an ultrafiltration membrane.

DESCRIPTION OF FIGURES

The file of this patent contains at least one drawing executed in color. Copies of this patent with color drawing(s) will be provided by the Patent and Trademark Office upon request and payment of the necessary fee.

FIG. 2 depicts the complete amino acid sequence of the recombinant procaspase 8 of the present invention.

DETAILED DESCRIPTION OF INVENTION

Figure 1A:
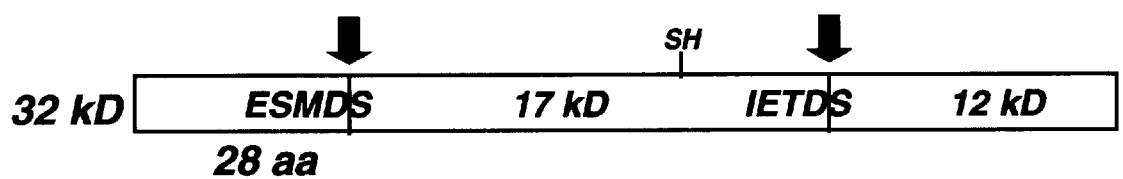
FIGS. 1A–1C depicts a schematic representation of native full length procaspase 8, procaspase 3, and of the recombinant procaspase 8 of the present invention lacking the death effector domains.
Figure 1B:
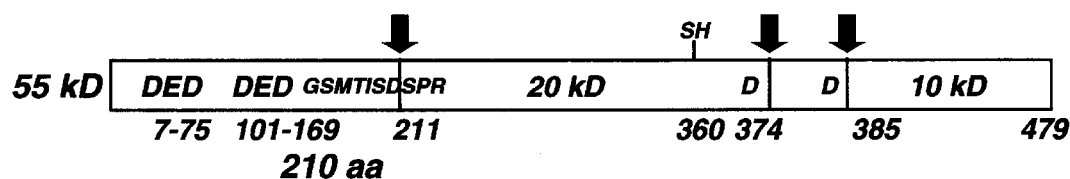
Figure 1C:
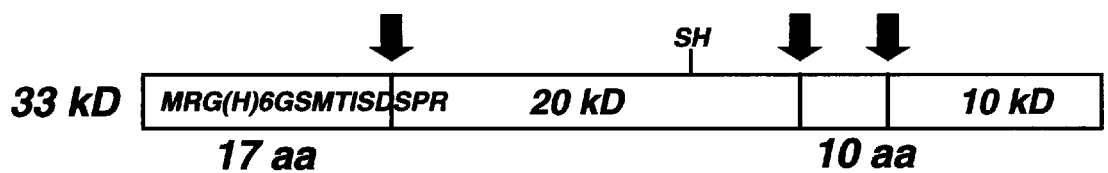

The present invention provides a procaspase 8 polypeptide construct lacking the death effector domain (DED) prodomain. Hereinafter, references to a"procaspase 8 construct" will be understood to refer to procaspase 8 polypeptide lacking the DED prodomain.

The invention also provides a method for the quantitative, reproducible conversion of the recombinant procaspase 8 protein construct to highly active human caspase 8. In our method, activation is achieved by concentration of the protein onto a matrix surface. Non-specific aggregation of our procaspase 8 construct, without the DED prodomain, at a matrix surface results in substantially complete activation of the proenzyme. We propose that this "matrix-assisted" activation of the proenzyme mirrors the mode of intracellular activation of procaspase 8. Because our proenzyme lacks the long N-terminal prodomain present in natural procaspase 8, yet is fully activable by surface aggregation, the prodomain present in native procaspase 8 may serve only to bring the catalytic prodomains into close proximity via binding of their death-effector regions to sites on activated membrane receptor complexes.

The complete amino acid sequence of the procaspase 8 protein construct is shown in FIG. 2 and SEQ ID NO: 1, and numbering of residues shown here will be used throughout the report in reference to particular amino acids in the construct.

The present invention also provides isolated nucleic acid molecules having a polynucleotide sequence encoding the procaspase 8 polypeptide lacking the DED prodomain polypeptides of the invention Thus, the isolated nucleic acid molecules provided by the present invention may differ, and yet encode identical amino acid sequences, due to the degeneracy of the genetic code. Isolated nucleic acid molecules comprising a nucleotide sequence encoding fragments of any of the above-mentioned polypeptides are also included herein.

As used herein, an "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

The DNA molecules encoding procaspase 8 polypeptide lacking the DED prodomain of the present invention include cDNA, chemically synthesized DNA, DNA isolated by PCR, genomic DNA, and combinations thereof.

In a preferred embodiment, the isolated nucleic acid molecule of the invention comprises a polynucleotide having the complete nucleotide sequence given in SEQ ID NO 2.

The materials and certain art recognized procedures utilized in achieving the present invention are the following. Restriction enzymes, T4 DNA Ligase, and cell culture media/antibiotics were from Life Technologies (Gaithersburg, Md.). Pfu cloned DNA polymerase was from Stratagene (La Jolla, Calif.). Oligonucleotide primers were synthesized by Genosys (The Woodlands, Tex.). Expression vectors, E. coli cells and DNA purification reagents were from Quagen (Chatsworth, Calif.). The DNA sequencing was done with the Sequenase Version 2.0 Kit from U.S.B. (Cleveland, Ohio). Guanidine hydrochloride, 7-amino-4-methyl-coumarin, 4-nitroaniline, Trizma base, Trizma hydrochloride, ethylenediaminetetraacetic acid tetrasodium salt, 2-mercaptoethanol, and dithiothrietol (99+%) were obtained from the Sigma Chemical Company. Mono and dibasic sodium phosphate were obtained from J. T. Baker. The caspase substrates Ac-DEVD-pNA, Ac-IETD-pNA, and Ac-IETD-AMC were obtained from California Peptide Research, Inc. (Napa, Calif.). The caspase substrates Ac-DEVD-AMC, Ac-YVAD-AMC and aldehyde inhibitors Ac-YVAD-H, Ac-DEVD-H and Ac-IETD-H were obtained from Peptide Institute, Inc. (Osaka, Japan; distributed in the US by Peptides International, Louisville, Ky.).

The cDNA coding for our procaspase 8 construct was amplified from Incyte clone T14775 by procedures known in the art (See, for example, K. Orth et al., J. Biol. Chem. 271, 20977–20980 (1996); S. M Srinivasula et al., Proc. Natl. Acad. Sci. U.S.A. 93, 14486–14491 (1996); M. Muzio et al., J. Biol. Chem. 272, 2952–2956 (1997) and cloned into the BamHI site of vector pGEX2T (Pharmacia) for expression. The insert was amplified by polymerase chain reaction (PCR), introducing a HindII site at the 3' end for directional cloning into the BamH1-HindIII sites of vector pQE30 (Qiagen). The primers used for PCR were 5'-ggg ctg gca agc cac gtt tgg tg (pGEX vector 5' sequencing primer) (SEQ ID NO: 3) and 5' ccg act caa gct tca atc aga agg gaa gac (SEQ ID NO: 4). Approximately 10 ng of the pGEX2T construct DNA was used under the following conditions: 5minutes denaturation at 90° C followed by 30 cycles of 30 seconds at 90° C, 30 seconds at 48° C. and 30 seconds at 72° C., and one cycle with a 5 minutes 70° C. extension. The PCR products were fractionated by agarose gel electrophoresis and purified by Geneclean (Bio101, Vista, Calif.). After digestion with BamHI and HindIII followed by agarose gel/Geneclean purification, the product was ligated into the corresponding sites of the pQE30 vector. The ligated DNA was used to transform E. coli M15 (pREP4) and DNA from potential positive colonies isolated using Qiaprep columns (Qiagen). Insert containing clones were identified by restriction digests and both DNA strands were sequenced.

The sequence of the new construct (pQE30-FLICE) is shown in SEQ ID NO: 2. The caspase 8 protease domain begins with $Met_{13}$ and terminates at $Asp_{286}$. A prosegment, consisting of the first 12 amino acids precedes the protease sequence and contains a $(His)_6$-tag for purification by Ni-chelate column chromatography.

The media used for plasmid progagation and expression was LB Broth with 100 µg/ml Ampicillin and 25 µg/ml Kanamycin, at 37° C. An overnight culture was diluted 1:100 and incubated with vigorous shaking to $A_{550}$=0.7–0.8. Expression was induced by the addition of IPTG to a final concentration of 1 mM. Cells were incubated for an additional 1,1, and 3 hours and overnight. Harvesting of the bacteria was done by centrifugation at 5000×g for 10 min at 4° C. The cell pellets were resuspended in TE (10 mM Tris HCl pH8.0, 1 nM EDTA) and frozen at −70° C. for protein purification.

The protein was obtained by resuspending the cells and disrupting them by sonication on ice using a Branson sonifier. The insoluble protein fraction was separated from the soluble proteins and most of the cell debris by low speed centrifugation (3000 RPM, SS34 Sorvall rotor) for 30 min.

Fractions were analyzed by SDS-PAGE. The presence of inclusion bodies was determined by light microscopy.

Quantitation of the protein was carried out by amino acid analysis. Samples were hydrolyzed in 6M HCl containing 1% phenol for 24 h at 110° C. in evacuated sealed tubes. Dried hydrolysates were dissolved in buffer at pH 2.2 (NaS; Beckman) prior to automated ion-exchange chromatography on a Beckman Model 6300 amino acid analyzer. As a secondary method of quantitation, protein was estimated using the Coomassie Plus™ protein assay (Pierce Chemical Co) against caspase 8 standards the concentration of which was determined accurately by quantitative amino acid analysis.

To analyze the protein sequence PTH-amino acid sequencing was performed using a Perkin Elmer/Applied Biosystems Procise™ sequencer. A MacIntosh Quadra 650 computer with PE/Applied Bisystems Procise™ Model 610A version 2.1 software was employed for data acquisition and processing.

The masses of major procaspase processing fragments and intermediates were determined with electrospray ionization on a Micromass Quattro II MS and MALDI ionization on a Perseptive Biosystems Voyager Elite time-of-flight MS. The masses, N-terminal sequence data and known amino sequence of the procaspase construct were used to confirm the sites of autocatalytic cleavage and thus the complete amino acid sequence of the fragments.

Figure 5:
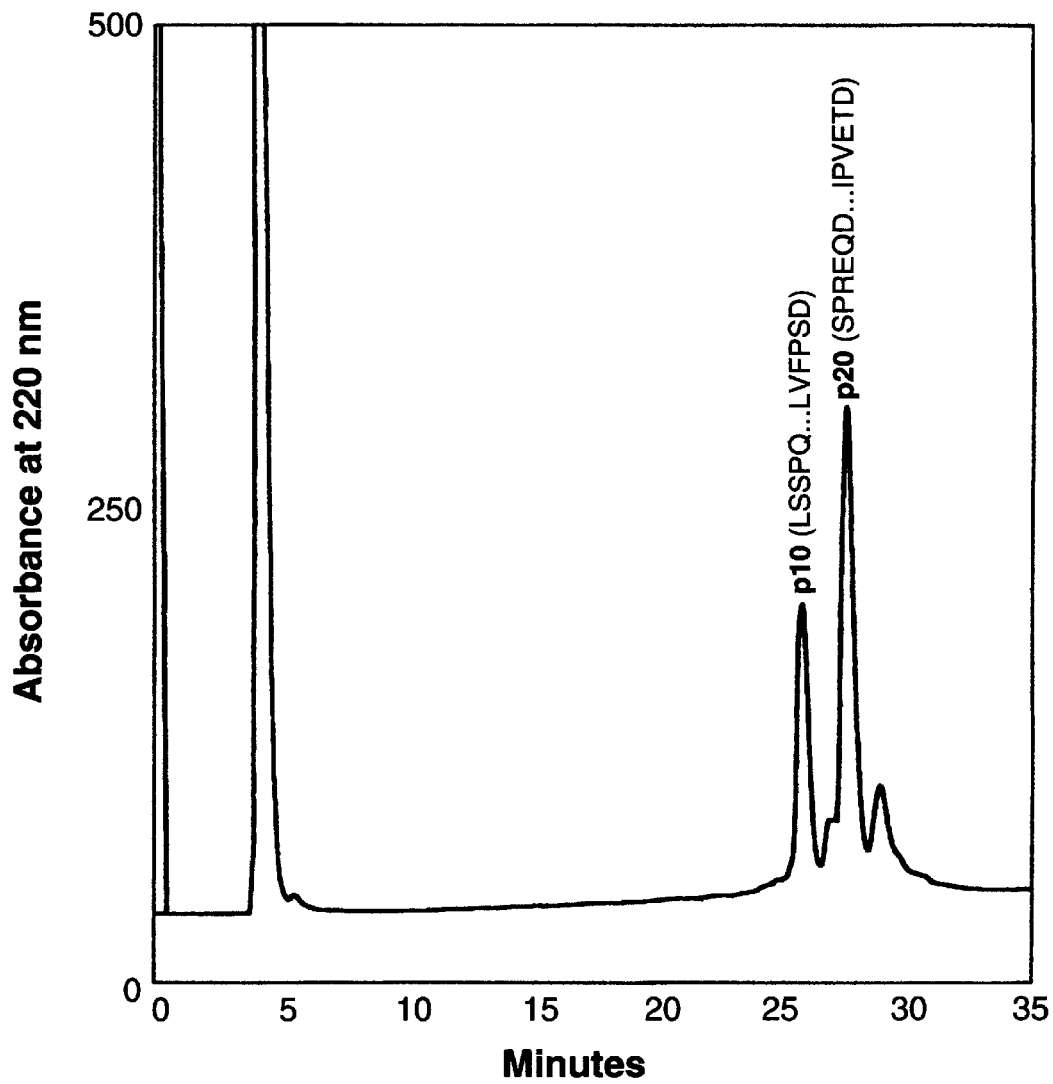
FIG. 5 shows the reversed phase HPLC separation of the 10 and 20 kDa subunits of activated caspase 8.

Processed caspase 8 was analyzed by reversed-phase HPLC on a Vydac protein $C_4$ column (0.46×25 cm), flow rate: 0.8 ml/min, mobile phase 25–50% B in 45 minutes (A: 0.15% TFA in water B: 0.15% TFA in acetonitrile) using a Perkin Elmer Series 410 bioLCpump and PE 235C diode-array detector. Detection wavelengths were 220 and 280 nm. Data were acquired, archived and analyzed on a Shimadzu Class-VP chromatography data system. The results ae shown in FIG. 5

Sodium dodecyl sulfate polyacrylamide gel electrophoresis (SDS-PAGE) was carried out using Novex 16% Tris-glycine or 10% NuPage Bis-Tris (with MES running buffer) precast mini-gels and a Novex Xcell II mini-cell apparatus. Samples were reduced and denatured by boiling in loading buffer containing 5% 2-mercaptoethanol prior to loading. Electrophoresis was carried out at constant voltage. Protein was visualized with Coomassie staining. Protein for N-terminal sequence analysis was electroblotted to PVDF (Amersham Hybond P) using the Novex Xcell 11 blot module. The results are shown in FIG. 3.

Enzyme activity of caspase 8 preparations was monitored using the chromogenic substrates Ac-DEVD-pNA or Ac-IETD-pNA or the fluorogenic substrates Ac-DEVD-AMC or Ac-IETD-AMC. For the chromogenic substrates, kinetic release of para-nitroaniline (pNA) was followed at 405 nm using either a Lambda 6 spectrophotometer or in a 3smicrotitre plate format using a Molecular Devices Thermomax plate reader with 405 nm wavelength filter. Kinetic enzyme assays monitoring the release of 7-amino-4-methyl-coumarin from the fluorogenic substrates were conducted using a Molecular Devices finax plate reader with Ex=355 nm and Em=460 nm.

Unless otherwise indicated, all specific enzyme activity measurements described herein were made using the Ac-DEVD-pNA substrate. Measurements were carried out at a substrate concentration of 400 $\mu$M ($K_m$=167 $\mu$M) in 100 mM sodium phosphate/10 mM Tris/100 mM DTT, pH 7.50 at 37° C. Initial rates were determined as follows: 100 $\mu$l of 1M DTT, 790 $\mu$l 100 mM sodium phosphate/10 mM Tris, pH 7.50, and 10 $\mu$l of caspase 8 sample solution (for protein concentrations near 0.5 mg/ml) were added to a quartz semi-micro cuvette. The solution was heated at 37° C. for 3 minutes after which time the reaction was started with the addition of 100 $\mu$l of 4 mM Ac-DEVD-pNA in 100 mM sodium phosphate/10 mM Tris, pH 7.50. Absorbance at 405 nm was followed for 15–30 using a Perkin Elmer Lamda 6 spectrophotometer with temperature controlled cuvette holder and auxiliary circulating water bath equilibrated to 37° C. Standards of paranitroaniline (pNA) were prepared to calibrate the molar extinction of the pNA product. Initial rate of pNA formation was calculated and specific activity ($\mu$mol pNA formed/min/mg) was calculated based on the protein concentration in each incubation mixture.

Figure 3:
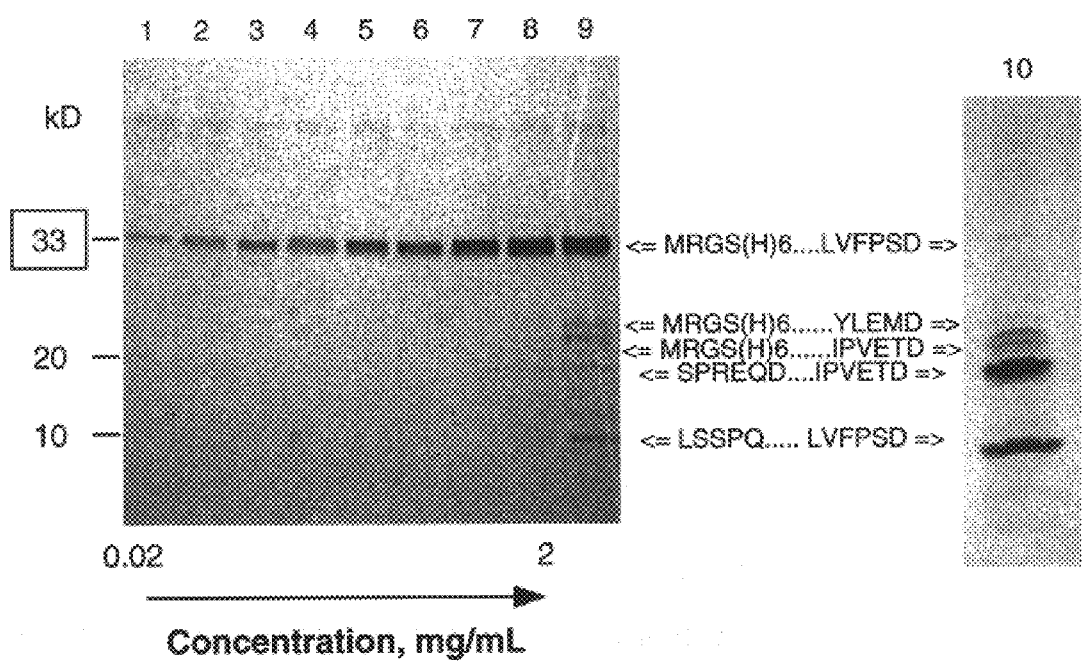
FIG. 3 is of an SDS-PAGEgel showing the effect of concentration of the buffered protein solution on enzyme activity and ultimate total processing under conditions of drying.
Figure 4:
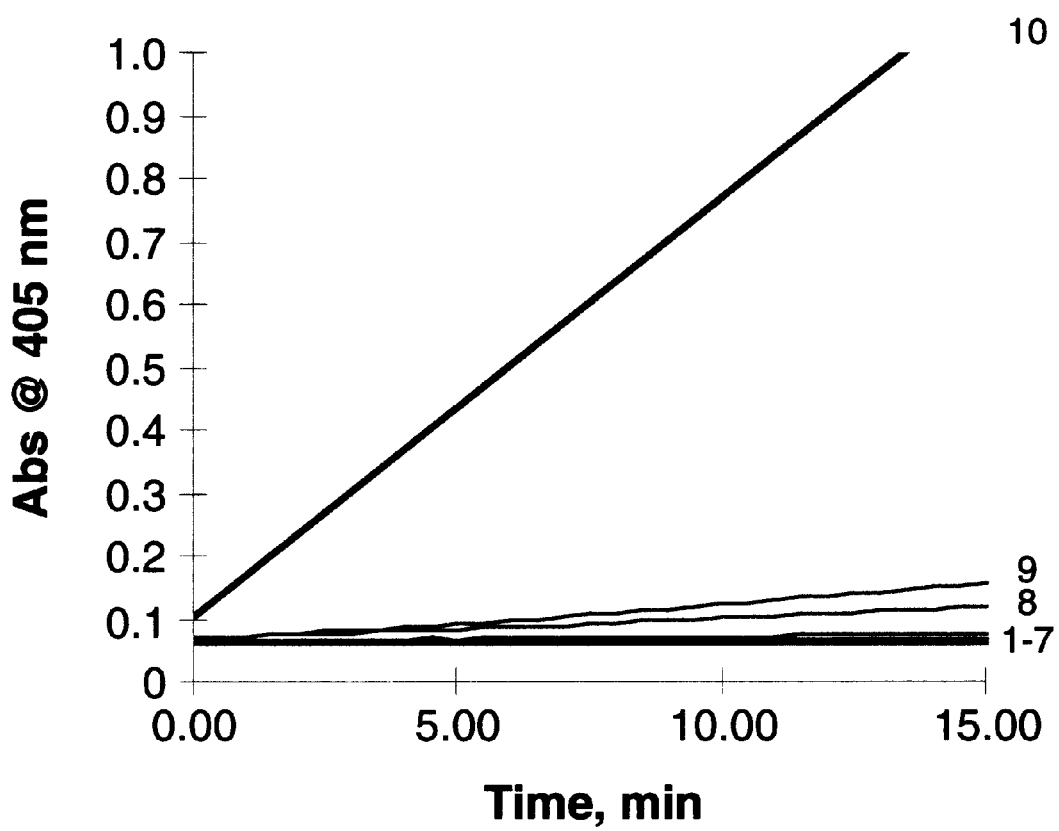
FIG. 4 is a graphic representation of the effect of concentration of the buffered protein solution on enzyme activity wherein the lines 1 to 10 correspond to lanes 1 to 10 of FIG. 3.

With the present invention we observed that upon dilution of the protein into 1.0 M Tris buffer, pH 8.0, the procaspase 8 gave a single, clean band on SDS-PAGE as shown in FIG. 3. The procaspase 8 at a concentration of about 25 $\mu$g/ml in 1.0 M Tris, pH 8.0/5 mM DTT, was concentrated under nitrogen pressure in an Amicon ultrafiltration cell, utilizing a regenerated cellulose 10000 MWCO membrane. Although we used an Amicon ultrafiltration cell which is cellulose based, other matrix surfaces may be used in practicing the present invention. During the course of concentration, samples were removed at various times and subjected to SDS-PAGE. Autoprocessing of the procaspase 8 to the characteristic 19 kDa and 11 kDa fragments of the active enzyme was not observed until a 100-fold concentration had been achieved (>2 mg/ml). Upon standing for up to 4 h at this concentration only minor levels of the 19 and 11 kDa bands were observed to form as can be seen in FIG. 3. Nevertheless, this low degree of processing was accompanied by generation of a corresponding low level of active enzyme, as seen by the hydrolysis of the chromogenic substrates Ac-Asp-Glu-Val-Asp-paranitroanilide or Ac-lle-Glu-Thr-Asp-paranitroanilide depicted in FIG. 4. To our surprise, rinses of the ultrafiltration membranes used for concentrating the protein showed low levels of caspase 8 of high specific enzyme activity. Consequently, concentration of the protein solution to near dryness was carried out, leaving a moist membrane. The ultrafiltration cell was then disassembled, and the amembrane washed with 1M Tris/5mM DTT, pH 8.0 buffer. All the protein was completely processed to the 19 and 11 kDa polypeptides as was shown by SDS-PAGE (see FIG. 3) and reversed phase HPLC (see FIG. 5). The yield of protein from this procedure was nearly quantitative. The overall yield from starting inclusion body protein was 50–75%, and it was reproducible. Complete conversion of our recombinant procaspase 8 protein to the highly active caspase 8 occurred consistently upon concentration of protein to near-dryness on ultrafiltration membranes. The completely processed enzyme showed a corresponding high level of activity (FIG. 4) with specific enzyme activities of 5–8 $\mu$mol/min/mg (Ac-DEVD-pNA) or 8.4 $\mu$mol/min/mg (Ac-IETD-pNA).

N-terminal sequence and sizes based upon mass spectral data for the two major 10 and 20 kDa autocatalytic processing fragments of our procaspase construct are annotated in FIG. 3. The minor ca 20 kD bands migrating above the major p19 band on the gel contain the N-terminal His tag leader sequence. Sequence analysis of these and other minor bands observed after protein was electroblotted to PVDF and visualized with Coomassie staining showed that they all derived from the p33 precursor and are not unrelated impurities. The full-length p33 precursor is indicated by the sequence: $M^1$ RGS(H)$_6$ . . . LVFPSD$^{286}$; residue number indications are as derived from the sequence of the whole construct given in FIG. 2. Prominent bands in lane 10 of FIG. 3 correspond to the major products of processing to give the 19 kDa peptide ($S^{18}PREQD \ldots IPVETD^{181}$) and the 11 kDa chain ($L^{192}SSPQ \ldots LVFPSD^{286}$). Minor bands designated in FIG. 3 correspond to incompletely cleaved intermediate fragments ($M^1RGS(H)_6 \ldots YLEMD^{191}$, $MRGS(H)_6 \ldots IPVETD^{181}$). Another site of alternate cleavage that was observed, but not shown in FIG. 3 is that represented by $S^{24}ESQTLD \ldots IPVETD^{181}$. The sites of autocatalytic activation that we observed were identical to those reported for full length procaspase 8 (S. M. Srinvasula, 1996, see above).

Our autocatalytically processed caspase 8 preparations readily cleaved the chromogenic caspase substrates Ac-DEVD-pNA or Ac-IETD-pNA, as well as the fluorogenic substrates Ac-DEVD-AMC or Ac-IETD-AMC. Concentrated, but unprocessed, protein had no measurable activity against the same substrates.

Specific Example 1, set forth below, provides details of the isolation and refolding of the recombinant protein, and it will be recognized by those skilled in the pertinent art that modifications to the procedure could be implemented. In the refolding process we maintained the pH of the solution at 8.0 using sodium hydroxide, however, other buffers having a pK in the range of 7 to 9 could be used. For example, phosphate, MOPS, HEPES are illustrative of suitable buffers which could be used. Also, in the solubilization of the recombinant protein formic acid could be used in place of glacial acetic acid, however, we prefer the use of glacial acetic acid. It is highly important to maintain the recombinant protein in the reduced state. The step of concentrating the recombinant protein on a matrix results in high yields (50–75%) of recombinant human caspase 8 enzyme having high specific activity.

The highly active human caspase 8 produced by the procedures of the present invention can be used for biochemical studies and x-ray crystallographic analysis. Active caspase 8 is an $\alpha_2\beta_2$ heterodimer, suggesting that therapeutic intervention in blocking the activity of this enzyme could derive from strategies geared both to blocking of the catalytic site, and to disruption of the dimer:dimer interaction.

The following specific example illustrates in detail the procedure for isolating the recombinant procasase 8 protein from inclusion bodies, refolding the protein and concentrating the protein to obtain active human caspase 8 protein.

EXAMPLE 1a

Refolding Protocol

E. coli expressing the construct as inclusion bodies were resuspended in 10 mM Tris, 1mM EDTA, pH 8.0 buffer to a cell density yielding $OD_{550}$ between 20–40. Cell aggregates were broken by brief (1–2 min) homogenization of the cell suspension using a polytron. A volume of 500 ml was passed through a Rannie high pressure homogenizer with a pressure differential of 10,000 psi to break up the cells. Inclusion bodies were sedimented by centrifugation at 1074×g for 30 min at 4° C. Inclusion body pellets were washed three times by resupension in 10 mM Tris, 1 mM EDTA, pH 8.0 buffer, and resedimentation by centrifugation at 1074×g. Inclusion bodies were then dissolved in 6M guanidine HCl, 0.1 M Tris, 5 mM DTT, pH 8.0 (2.5 ml per every 10 ml of TE buffer that was used for original E. coli suspension). The inclusion bodies were allowed to dissolve with magnetic stirring on ice for 1 hour followed by centrifugation at 27,491×g for 15 min at 4° C. to sediment undissolved solid.

A volume of 20 ml of glacial acetic acid was added to 20 ml of the 6M guanidine solubilized inclusion bodies (procaspase 8 protein concentration of 1.6 mg/ml by quantitative amino acid analysis). The chaotrope was removed by dialysis (12–14,000 MWCO) overnight against 2l of 50% acetic acid followed by dilution into 360 ml of Milli-Q purified water. This solution was rapidly diluted into 1600 ml of 1M Tris, 5 mM DTT, pH 8.0. The pH of the solution was adjusted to 8.0 with 2N sodium hydroxide. The solution, 2450 ml, was transferred to an Amicon Model 2000 stirred ultrafiltration cell with a MilliPore PLGC 10,000 MWCO regenerated cellulose, low protein binding 150 nmm diameter membrane. The solution was concentrated with stirring under a nitrogen pressure of 40 psi. Specific activity measurements and SDS-PAGE analysis were performed as a function of concentration of the 32 kD proenzyme construct. The solution was concentrated from 2450 mnl to near dryness, leaving a moist membrane. Protein was then resolubilized with the addition of 40.0 ml of fresh 1M Tris15 mM DTT pH 8.0 buffer. Undissolved material was removed by centrifugation and protein measured by quantitative amino acid analysis.

EXAMPLE 1b

Size Exclusion Chromatography

Recombinant activated human caspase 8 (0.5 mg/mnl) was analyzed by size exclusion chromatography (injected volume=20 μl) at 25° C. on a Toyapearl G2000SW column (300×8 mm;Toso Haas) with Dulbecco's phosphate buffered saline, pH 7.1 as the running buffer (Gibco BRL, without $MgCl_2$ and $CaCl_2$) at a flow rate of 0.5 ml/min. Chromatography was carried out on a Waters 625 HPLC system with Waters 484 variable wavelength detector (UV@220 nm). Data were acquired, archived and analyzed on a Shimadzu Class-VP chromatography data system. Fractions (100 μl each) eluting from the gel filtration column were collected manually. The fractions were assayed immediately following collection for enzyme activity in the following manner: 50 μl of each column fraction was added to separate wells of a 96-well microtitre plate, 20 μl of 1M DTT, and 125 μl of 100 mM sodium phosphate, pH 7.2 buffer was added. The plate was preincubated at 37° C. for 3 min and then 5 μl of 4 mM Ac-IETD-pNA substrate stock in buffer was added to each well to start the reactions. The initial rates of reaction were followed by monitoring absorbance change at 405 nm. Molecular weight calibration was performed using the following standards obtained from Sigma: BSA (66,000), ovalbumin (45,000), chymotrypsinogen A (25,000), cytochrome c (12,500).

Samples of activated caspase 8 in 1M Tris, pH 8.0 containing 5, 25, and 100 mM DTT were allowed to stand on ice for up to 48 h. Aliquots were analyzed by size exclusion chromatography and enzyme activity (as above).

What is claimed is:

1. A method for converting recombinant procaspase 8 protein lacking the DED to active human caspase 8 enzyme which comprises passing a solution of said protein through a matrix capable of concentrating said protein to affect auto-activation thereof to give active human caspase 8 enzyme wherein the procaspase 8 protein lacking the DED comprises the amino acid sequence of SEQ ID NO: 1.

2. A method for converting recombinant procaspase 8 protein lacking the DED to active human caspase 8 enzyme which comprises passing a solution of said protein through a cellulose matrix capable of concentrating said protein to affect auto-activation thereof to give active human caspase 8 enzyme wherein the procaspase 8 protein lacking the DED comprises the amino acid sequence of SEQ ID NO: 1.

* * * * *

SEQUENCE LISTING

<160> NUMBER OF SEQ ID NOS: 4

<210> SEQ ID NO: 1
<211> LENGTH: 286
<212> TYPE: PRT
<213> ORGANISM: Homo sapiens

<400> SEQUENCE: 1

Met Arg Gly Ser His His His His His His Gly Ser Met Thr Ile Ser
 1               5                  10                  15

Asp Ser Pro Arg Glu Gln Asp Ser Glu Ser Gln Thr Leu Asp Lys Val
            20                  25                  30

Tyr Gln Met Lys Ser Lys Pro Arg Gly Tyr Cys Leu Ile Ile Asn Asn
        35                  40                  45

His Asn Phe Ala Lys Ala Arg Glu Lys Val Pro Lys Leu His Ser Ile
    50                  55                  60

Arg Asp Arg Asn Gly Thr His Leu Asp Ala Gly Ala Leu Thr Thr Thr
65                  70                  75                  80

Phe Glu Glu Leu His Phe Glu Ile Lys Pro His Asp Asp Cys Thr Val
                85                  90                  95

Glu Gln Ile Tyr Glu Ile Leu Lys Ile Tyr Gln Leu Met Asp His Ser
            100                 105                 110

Asn Met Asp Cys Phe Ile Cys Cys Ile Leu Ser His Gly Asp Lys Gly
        115                 120                 125

Ile Ile Tyr Gly Thr Asp Gly Gln Glu Ala Pro Ile Tyr Glu Leu Thr
    130                 135                 140

Ser Gln Phe Thr Gly Leu Lys Cys Pro Ser Leu Ala Gly Lys Pro Lys
145                 150                 155                 160

Val Phe Phe Ile Gln Ala Cys Gly Gly Asp Asn Tyr Gln Lys Gly Ile
                165                 170                 175

Pro Val Glu Thr Asp Ser Glu Gln Pro Tyr Leu Glu Met Asp Leu
            180                 185                 190

Ser Ser Pro Gln Thr Arg Tyr Ile Pro Asp Glu Ala Asp Phe Leu Leu
        195                 200                 205

Gly Met Ala Thr Val Asn Asn Cys Val Ser Tyr Arg Asn Pro Ala Glu
    210                 215                 220

Gly Thr Trp Tyr Ile Gln Ser Leu Cys Gln Ser Leu Arg Glu Arg Cys
225                 230                 235                 240

Pro Arg Gly Asp Asp Ile Leu Thr Ile Leu Thr Glu Val Asn Tyr Glu
                245                 250                 255

Val Ser Asn Lys Asp Asp Lys Lys Asn Met Gly Lys Gln Met Pro Gln
            260                 265                 270

Pro Thr Phe Thr Leu Arg Lys Lys Leu Val Phe Pro Ser Asp
        275                 280                 285

<210> SEQ ID NO: 2
<211> LENGTH: 870
<212> TYPE: DNA
<213> ORGANISM: Homo sapiens

<400> SEQUENCE: 2
atgagaggat cgcatcacca tcaccatcac ggatccatga caatctcgga ctctccaaga    60
gaacaggata gtgaatcaca gactttggac aaagtttacc aaatgaaaag caaacctcgg   120
ggatactgtc tgatcatcaa caatcacaat tttgcaaaag cacgggagaa agtgcccaaa   180

```
cttcacagca ttagggacag gaatggaaca cacttggatg cagggycttt gaccacgacc      240
tttgaagagc ttcattttga gatcaagccc cacgatgact gcacagtaga gcaaatctat      300
gagattttga aaatctacca actcatggac cacagtaaca tggactgctt catctgctgt      360
atcctctccc atggagacaa gggcatcatc tatggcactg atggacagga ggcccccatc      420
tatgagctga catctcagtt cactggtttg aagtgccctt cccttgctgg aaaacccaaa      480 gtgttttta ttcaggcttg tcagggggat aactaccaga aaggtatacc tgttgagact       540
gattcagagg agcaaccta tttagaaatg gatttatcat caactcaaac gagatatatc       600
ccggatgagg ctgactttct gctgggatg gccactgtga ataactgtgt ttcctaccga       660
aaccctgcag agggaacctg gtacatccag tcactttgcc agagcctgag agagcgatgt      720
cctcgaggcg atgatattct caccatcctg actgaagtga actatgaagt aagcaacaag      780
gatgacaaga aaacatggg gaaacagatg cctcagccta ctttcacact aagaaaaaaa       840
cttgtcttcc cttctgattg attgaagctt                                       870

<210> SEQ ID NO: 3
<211> LENGTH: 23
<212> TYPE: DNA
<213> ORGANISM: Homo sapiens

<400> SEQUENCE: 3
gggctggcaa gccacgtttg gtg                                               23

<210> SEQ ID NO: 4
<211> LENGTH: 30
<212> TYPE: DNA
<213> ORGANISM: Homo sapiens

<400> SEQUENCE: 4
ccgactcaag cttcaatcag aagggaagac                                        30
```